United States Patent [19]
Curtis et al.

[11] Patent Number: 4,832,759
[45] Date of Patent: May 23, 1989

[54] MICROSTRUCTURES

[75] Inventors: Adam S. G. Curtis; Christopher D. W. Wilkinson, both of Glasgow, Scotland

[73] Assignee: The University Court of the University of Glasgow, Glasgow, Scotland

[21] Appl. No.: 220,413

[22] Filed: Jul. 19, 1988

Related U.S. Application Data

[63] Continuation of Ser. No. 106,988, Oct. 5, 1987, abandoned, which is a continuation of Ser. No. 675,206, Nov. 27, 1984, abandoned.

[30] Foreign Application Priority Data

Nov. 29, 1983 [GB] United Kingdom ................. 8331865

[51] Int. Cl.$^4$ .............................................. C12M 3/00
[52] U.S. Cl. .................................... 435/285; 435/287
[58] Field of Search ....................... 435/284, 285, 287

Primary Examiner—Alan Cohan
Attorney, Agent, or Firm—Stephen G. Rudisill

[57] ABSTRACT

The present invention relates to the location of biological cells 5 in a predetermined spatial disposition relative to each other on a solid non-biological substrate. According to the invention an extended generally planar surface of the substrate is provided with a plurality of surface discontinuities 4 at least partly defining cell adhesion enhanced and/or cell-adhesion orienting zones having a width of from 0.2 to 20 micrometers in a predetermined relation to each other and substantially spaced apart from each other. When a plurality of the cells 5 in a physiologically acceptable medium is brought into contact with said substrate surface cells attached to the substrate surface preferentially and/or in preferential orientations at said discontinuities 4.

10 Claims, 2 Drawing Sheets

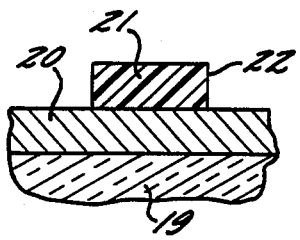
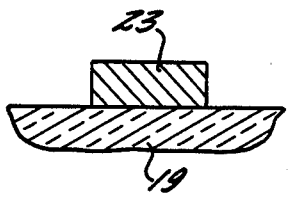
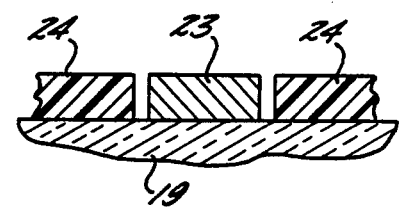
fig. 7A.  fig. 7B.  fig. 7C.
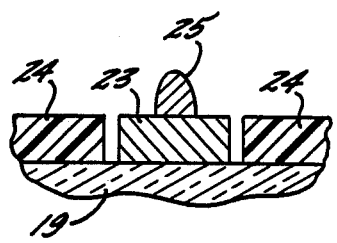
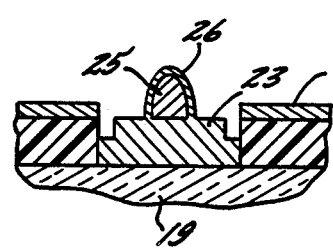
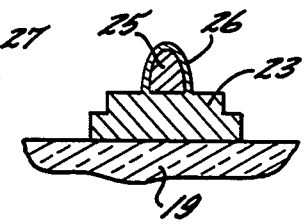
fig. 7D.  fig. 7E.  fig. 7F.
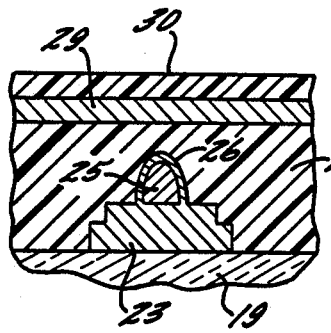
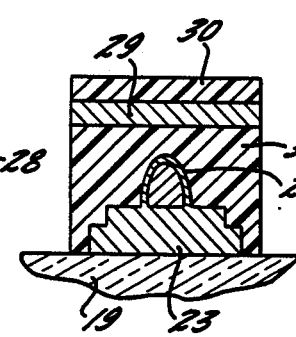
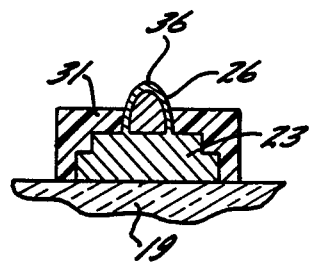
fig. 7G.  fig. 7H.  fig. 7I.

MICROSTRUCTURES

This is a continuation of co-pending application Ser. No. 106,988, filed on 10/5/87, which is a continuation of Ser. No. 675,206, filed 11/27/84, both now abandoned.

This invention relates to bio-mechanical microstructures and the formation thereof.

The study of the functioning and operation of biological tissues at sub-cellular and inter-cellular levels and the utilization thereof in artificial devices requires the formation of bio-mechanical microstructures with predetermined interconnections between individual cells and non-biological substrates. Whilst some progress in this direction has been made at a microscopic level this has in general been simply at a gross structural level e.g. bone and valve prostheses, and has not permitted utilization of the topographical features of individual cells.

It is an object of the present invention to avoid or minimize the problems of achieving such interconnections and in particular to provide bio-mechanical structures with cells attached to non-biological substrates in predetermined spatial dispositions relative to each other.

The present invention provides a method of locating a plurality of cells in a predetermined spatial disposition relative to each other on a solid non-biological substrate, which method comprises providing on an extended generally planar surface of said substrate a plurality of surface discontinuities at least partly defining cell-adhesion enhanced and/or cell-adhesion orienting zones having a width of from 0.2 to 20 micrometers in a predetermined relation to each other and substantially spaced apart from each other, and bringing a plurality of said cells in a physiologically acceptable medium into contact with said substrate surface.

The present invention also extends to a bio-mechanical micro-structure comprising a solid non-biological substrate with an extended generally planar surface on which surface is provided a plurality of surface discontinuities at least partly defining cell-adhesion enhanced and/or cell-adhesion orientating zones having a width of from 0.2 to 20 micrometers in a predetermined relation to each other and substantially spaced apart from each other with a plurality of cells attached to said zones of said surface.

In another aspect the present invention provides a solid non-biological substrate suitable for use in the formation of bio-mechanical micro-structures, which substrate has an extended generally planar surface with a plurality of surface discontinuities at least partly defining cell-adhesion enhanced and/or cell-adhesion orientating zones having a width of from 0.2 to 20 micrometres in a predetermined relation to each other and substantially spaced apart from each other.

The privision of such surface discontinuities is believed to control cell-adhesion and/or locomotion or extension by causing the cells to assume certain orientations relative to said said discontinuities, by facilitating topographical interactions between the cells and the substrate surface, and the provision of such discontinuities in predetermined dispositions permits the construction of predetermined arrays of cells which in turn facilitates control of interfacing between individual cells and non-biological micro-structures including non-biological electrical circuits as well as amongst the cells themselves.

As used herein the term "discontinuity" indicates any form of surface irregularity including for example ridges with rounded edges i.e. which do not actually include a mathematical discontinuity. Amongst the various forms of surface discontinuity that may be used in accordance with the present invention are steps, grooves and generally rectangular section ridges, of various lengths, including such features whose length is comparable to their width that is to say generally circular or polygonal protuberances and recesses, including also recesses which extend through the substrate to its other side i.e. bores. Moreover where the discontinuities are substantially elongate these may be generally rectilinear or in some cases preferably arcuate including in particular spiral especially logarithmic spiral. spiral discontinuities have the advantage that cells which become attached thereto tend to migrate along them to that part having the greatest radius of curvature. Thus it is possible to achieve location of a cell at a particular point viz. the radially outer end of the spiral irrespective of the initial point of attachment. In addition two or more discontinuities may be interconnected with one another e.g. so as to form branched discontinuities. In general the discontinuities will have a height or depth of at least 5 nm and possibly up to several hundreds of micrometers. Preferably, though the discontinuities will have a height or depth of from 50 nm to 2 to 3 $\mu$m.

Whilst the bio-mechanical structures of the present invention may include various biological cells, preferred cells are those having cytoskeletons which are polarised to at least some extent and not appreciably labile. Suitable cells include nerve cells, fibroblasts and glial or neurologiial cells, whilst relatively labile and/or non-polarised cytoskeleton cells such as leucocytes, lymphocytes and macro-phages are generally not suitable. It may also be noted that the cells may be attached to the substrate at desired locations either directly or via processes thereof such as dendtites in the case of nerve cells. In addition it should be noted that due to the differences in size and topography between different cells, different degrees of cell-adhesion may be obtained for any given discontinuity configuration, size, and surface material so that particular combinations of these features may be preferred for certain types of cells. Moreover even if an adequate degree of cell-adhesion can be obtained it is generally desirable to avoid configurations which result in the cell adopting a significantly strained or unnatural configuration since this may interfere with the normal functioning of the cell, although in some cases a limited degree of cell deformation may in fact be advantageous e.g. in facilitating attachment at a specific point on the substrate.

The substrate may in general be of any convenient solid material provided that the substrate surface at said discontinuities is generally inert and non-toxic towards cells attached thereto and does not substantially inhibit cell-adhesion thereto. Suitable materials include silica and various glasses, various silicones, epoxy resins, polytetrafluoroethylene, polyamides, partly hydroxylated polyamides, polyolefins, and polystyrene, polyimides, polymethacrylates, cellulose and reconstituted celluloses, graphite, carbon fibre, and metals and metal oxides such as those mentioned hereinbelow.

Whilst in some cases it may be sufficient merely to orientate certain of the cells attached to the substrate surface, it may in other cases be desired to enhance cell adhesion at specific locations (possibly irrespective of orientation) and/or positively inhibit cell-adhesion at other locations. Advantageously therefor the method of the invention includes the step of providing at at least part of said substrate surface away from said discontinuities, with cell-adhesion inhibiting material, for example an inert plastics material, for example pure n-paraffin wax, polystyrene or polypropylene in their conventional untreated forms as well as untreated polyolefins in general, partially hydrolysed polyvinylacetate, and polymeric materials with highly negatively charged surfaces e.g. highly nitrated cellulose nitrate and carboxymethyl cellulose.

Alternatively or additionally the substrate is preferably selectively provided at said discontinuities with cell-adhesion promoting material. Suitable cell adhesion promoting materials that may be mentioned include for example silica, graphite, carbon fibre, metal e.g. gold, palladium, platinum and iridium, metal oxides such as alumina, and titanium, molybdenum, and tantalum oxides, including surface layers of such oxides formed on the corresponding metal, and suitably trated plastics materials for example polypropylene or polystyrene treated so as to provide a plurality of hydroxyl groups on its surface, e.g. from 500 to 6000 hydroxyl groups per 1000 $nm^2$, partly hydroxylated polyimides, polyamides and polymethacrylates treated so as to bear surface hydroxyl andor amino groups.

It should also be noted that although some materials can provide an acceptable degree of cell-adhesion thereto they are undesirable for other reasons e.g. due to undesired chemical interactions with cells leading to poisoning thereof Such materials include gallium arsenide and copper and should therefore normally be avoided in the biomechanical structures of the present invention. Other materials such as untreated polystyrene tend to preferentially absorb proteins such as $\alpha$-1-trypsin which may be present in cell media such as serum and which may interfere with cell-adhesion to the substrate to a greater or lesser extent.

Preferably the substrate is provided at said discontinuities with one or more projections of an electrical conductor or semi-conductor material having a transverse width in the range of from 0.2 to 20 micrometers and a generally similar height. Most preferably these projections are formed and arranged so as to be more or less phagocytosable by the cells to be attached thereat. The surface discontinuities may be formed by an suitable means for the formation of the desired type of discontinuity. Thus, for example, in the case of grooves these may be produced with the aid of suitable guided finely focused laser beams or ion beams e.g. oxygen ion beams. Preferably though most forms of discontinuity are produced by lithographic means. These generally involve the formation of a suitable pattern in a photo, electron, or X-ray sensitive resist and the subsequent realisation of a relief structure in the desired material by subtractive and/or additive means. In a subtractive processing step the desired material is present under the resist before exposure and after exposure is etched by liquid or gaseous phase means including e.g. ion-beam etching, whilst in an additive processing step the desired material is added after the formation of the relief pattern in resist by for example vacuum depositon or by plating e.g. electro-plating.

Naturally the present invention also extends to a bio-mechanical structure when made by a method of the invention.

The bio-mechanical structures of the present invention have various applications including facilitating the study of individual cells and cell systems comprising small numbers of cells, especially nerve cells e.g. so-called nets of nerve cells, with particular regard to their mode of functioning and operation both at intra and inter-cellular levels, as well as in prosthetic devices, in particular sensory aided prostheses and externally (electrically) driven biological structures.

Further preferred features and advantages of the present invention will appear from the following detailed description given by way of example of some preferred embodiments illustrated with reference to the accompanying drawings wherein:

FIGS. 7A to 7I illustrate principal stages in a process for the production of a substrate structure of the invention;

Figure 1:
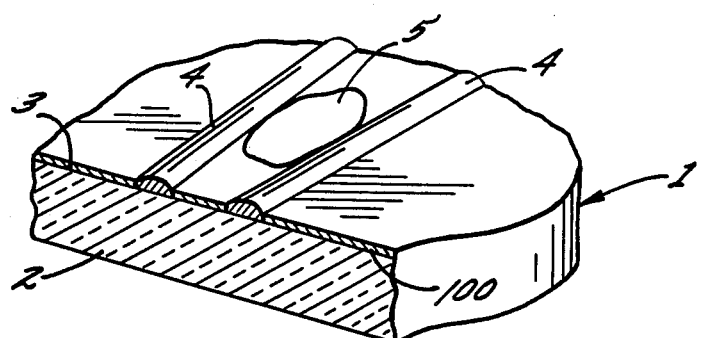
FIG. 1 is a generally schematic perspective view of a first embodiment of a bio-mechanical structure of the invention.

FIG. 1 shows a bio-mechanical micro-structure 1 of the invention comprising a fused silica substrate 2 in the form of a small plate. On the upper surface 3 are provided two spaced apart and diverging ridge structures 4 in the form of gold fingers each having a width of 6 $\mu$m and a thickness of 0.4 $\mu$m. The spacing between the fingers 4 ranges from 2 to 20 $\mu$m and they are formed on the surface 3 by ion beam etching of gold. On either side of the gold fingers 4 the silica substrate is optionally coated with a layer of untreated polystyrene 100 having a thickness of about 0.1 $\mu$m. The polystyrene coating 100 is applied to the silica surface 3 by evaporation from toluene solution.

A suspension of nerve cells cultured from chick embryo brain (2-10$\times 10^4$ cells per ml of aqueous solution containing Ham's FlO saline with 1% foetal calf serum and additions of transferrin, insulin, and nerve growth factor) was then applied to the above-described substrate surface and maintained in contact therewith for 60 minutes at 37° C. The excess solution was then drained off and the substrate washed with fresh culture medium.

Inspection of the substrate then showed that a number of nerve cells 5 had become selectively attached thereto at the gold wires and in particular across adjacent pairs of converging gold wires.

Figure 2:
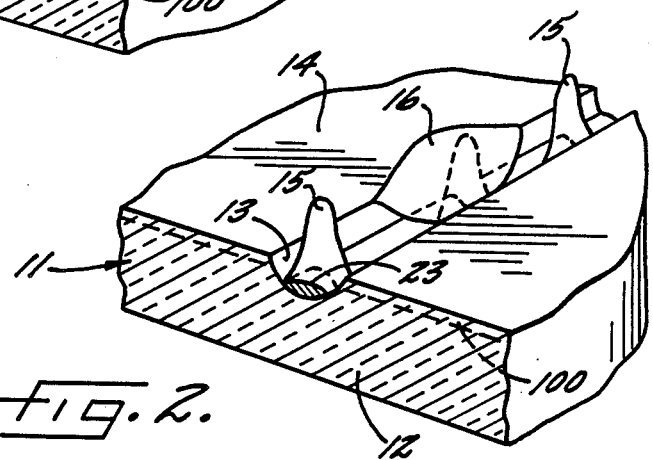
FIG. 2 is a similar view of a second embodiment.
Figure 3:
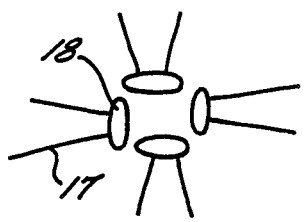
FIGS. 3 to 6 are plan views of some further embodiments.
Figure 4:
Figure 5:
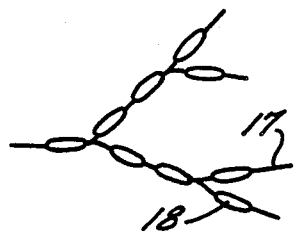
Figure 6:
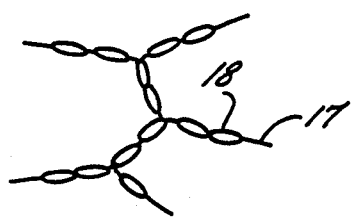

FIG. 2 shows another bio-mechanical microstructure comprisng a fused silica substrate 12 with a groove 13 etched in its upper surface 14 by means of argon iron beam etching through a photomicrographically defined photoresist layer.

Within the groove, which has a width of about in the range 0.5 to 10 $\mu$m is provided a plurality of upstanding projections 15 formed of gold.

Each projection 15 has a height of some 0.1 to 0.5 $\mu$m and a thickness of about 0.02 to 0.1 $\mu$m.

The projections are desirably formed so as to have a substantially smooth surface so that they penetrate the cell wall readily and the cell wall seals around the projections. The projections may be formed by any suitable photolithographic technique. Conveniently the projections may be formed by depositing a thin layer (20–30 nm) of gold or other metal onto a hydrocarbonpolymer pillar formed by polymerisation effects of an electron beam in vacuo making use of traces of organic materials from the vacuum pump oil of the pump used to produce the vacuum (Broers (1)).

Nerve cells 16 are applied to the substrate surface in a similar manner to that described above and become attached to the groove 13. As shown in the drawing certain projections 15 become phagocytosed by the cell providing a direct mechanical and electrical connection with the cell interior.

If desired electrical conductor or semi-conductor material tracks or other structures may be provided within the grooves and/or extending outside the grooves a cell-adhesion inhibiting coating may be provided.

FIGS. 3 to 6 show various different arrangements of pluralities of grooves 17 and which can be used to define desired networks of cells 18.

Figures 8, 9:
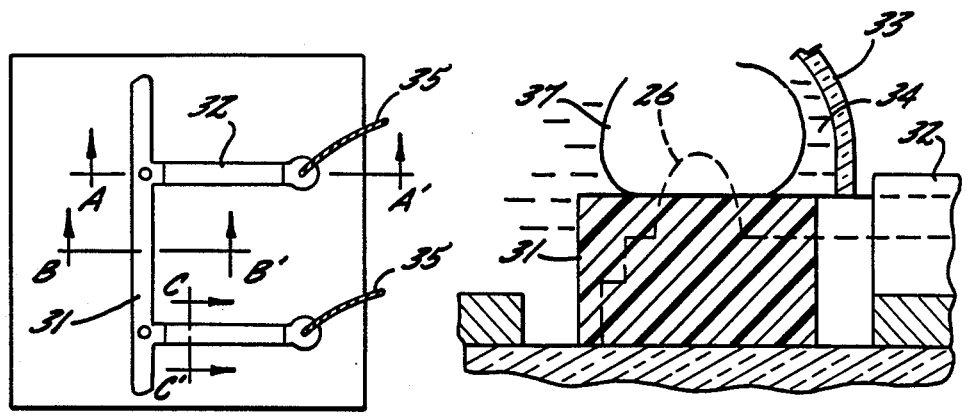
FIG. 8 is a plan view of a structure produced by the process of 7A to 7I.
FIGS. 9, 10 and 11 are vertical sections along the lines B-B', A-A', and C-C', in FIG. 8 respectively.
Figure 10:
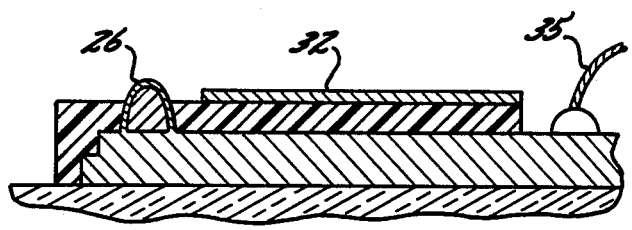

FIGS. 7A to 7I illustrates schematically the principal stages in a suitable lighographic manufacturing process for the production of another substrate structure further illustrated in FIGS. 8 to 10, suitable for use in making direct electrical connections with the interior of a cell. Since the basic lithographic techniques employed in the process are known in the art they will only briefly be described.

Aluminium metal was evaporated over a glass substrate 19 to form a metal layer 20 of approximately 50 nm thickness. This was then overcoated with a layer of photoresist 21 of similar thickness and exposed through a mask (not shown) defining the pattern of leads to the probes (see below). The photoresist 22 was then developed to produce a protective pattern 22 as shown in FIG. 7A which after chemical etching of the unprotected metal 20 and subsequent removal of the resist pattern 22, left a metallic lead pattern 23 as shown in FIG. 7B. Photoresist was then coated onto the processed substrate surface and exposed to the negative of the first mask to leave, after development resist 24 everywhere but on the metal lead pattern 23 as shown in FIG. 7C. Needle-shaped columns 25 of polymerised contamination are then formed at desired spots on the conductor tracks 23 (See FIG. 7D) by focussing an electron beam on said spots. The columns 25 of material so formed have a diameter a few times the beam diameter and their height can be made many times the beam diameter (Broers (1)). Any residual hydrocarbons in the vacuum are polymerised by the electron beam.

The processed substrate is then overcoated with metal so that probe is now metallised 26 and electrically connected to the conductor track pattern 23 (see FIG. 7E). The photoresist 24 is then dissolved in a strong solvent thus removing the resist together with the unwanted metal 27 on top of it (see FIG. 7F). The resulting processed substrate is then overcoated with polyimide and baked at 350° C. to form an insulating layer 28 having a thickness greater than the contained height of the conductor track 23 and metallised probe 26 thereon. The polyimide is used in two roles viz to form the ridge to which the cells adhere and to provide an insulator for the probe leads. The polyimide layer 28 is then overcoated first with Aluminium 29 and then with photoresist 30 (see FIG. 7G) and exposed via a mask defining a polyimide ridge pattern. After development of the photoresist and chemical etching of the aluminium through the photoresist pattern, the processed substrate is placed in a reactive oxygen plasma and the polyimide not protected by aluminium etched away to leave a polyimide ridge pattern 3 with substantially vertical walls (See FIG. 7H). The protective aluminium layer 29 having served its purpose as an oxygen plasma etch mask, it is removed by chemical etching and the processed substrate then returned to the oxygen plasma etcher and more polyimide removed until the probes 26 stand proud of the polyimide ridges 31 (see FIG. 7I).

The processed substrate is then overcoated with resist and exposed to a further mask defining an electrical screen pattern. After development of the resist overcoating by another metal layer and lift-off of resist pattern and unwanted metal thereon, the metal screen layer 32 will cover the whole specimen except for the cell-supporting polyimide ridges and the contact pads (see FIGS. 10 and 11 in particular). Finally a selection of glass tube 33 is glued on to the processed substrate to separate the central biological area containing cell support medium 34 and which will therefore be wet—from the surrounding electrical area. By this means the probe leads 36, which are connected to the remote ends of the conductor tracks 23, are electrically isolated from the saline solution cell support medium 34 by a ground plane everywhere except for a few micrometers close to the metallized probe 26. Even here only the tip 36 of the probe will not be insulated and this will be isolated from the medium 34 once it is phagocytosed by a cell 37 attaching to the cell-support polyimide ridge 31 (see FIG. 9). FIG. 12 shows schematically a further substrate structure of the invention produced using photo-lithographic procedures with ion beam milling through suitable masks to form a series of logarithmic spiral grooves 40 in the surface 41 of a glass plate 42. The grooves 40 were ten micrometers wide and half a micrometer deep. The smallest (innermost end 43) radius of curvature of the spiral was 20 micrometers and the largest (outermost end 44) two hundred and fifty micrometers. BHK fibroblast cells 45 were applied on to this substrate in a serum containing culture medium (Eagle's MEM medium with 10 percent tryptose-phosphate broth and ten percent calf serum) and cultured at 37° C. for two days. During this period the areas containing the spirals 40 were filmed by time-lapse video recording using phase contrast microscopy and a very low light level video camera, the latter being used in order to minimise any possible adverse effect of light or heat radiation from the microscope lamp. The cells were observed locate at the groove within as little as 15 to 30 minutes and take up a spread shape on the groove edges 46 related to the radius R of the spiral 40 at that region. Cells 47 on the small radius end 43 of the groove 40 did not spread properly and remained immobile. Cells 48 settling on wider radii sections elongated to an extent related to the radius of curvature at that region and migrated outwardly along the groove edges 46 to the end of greatest radius 44.

Further possible uses of bio-mechanical structures of the invention, particularly those including cell-adhesion enhanced zones, include the separation of cells from other biological material and/or the fractionation of different types of cells on the basis of differences in morphology and cyto-skeleton lability, the cells and/or particular types of cells being preferentially retained by the substrate to which the mixture of interest has been applied whilst other components of the mixture are eluted out of the system.

Figure 11:
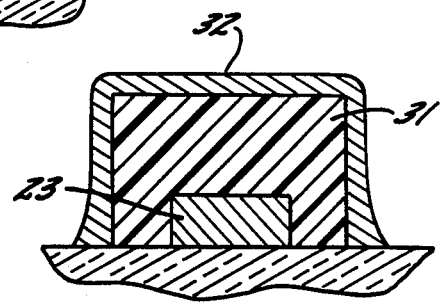
Figure 12:
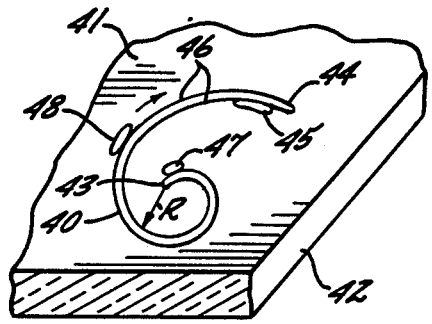
FIG. 12 is a plan view of a spiral groove structure of the invention.

With reference to the embodiment of FIGS. 7 to 11 and in particular the shielding of the conductor tracks 23 as illustrated in FIG. 11 it should be noted that the polyimide (or other suitable dielectric) sheath 31 should be dimensioned relative to the dimensions of the conductor tracks 23 and outer metal shielding 32 and the dielectric properties of the sheath so as to obtain a suitable characgteristic impedance for this electrical connection. Desirably the connection should have a characteristic impedance in the range from 25 to 200 ohms. In the specific example shown (note: FIGS. 7 to 11 are not drawn to scale) the conductor track 23 conveniently has a thickness of about 0.2 µm, the polyimide insulation sheath 31 a thickness in the region of 1 to 2 µm, and the outer conductor shield 32 a thickness of about 0.3 µm.

Literature Reference (1):
App. Phys. Lets. 29 296–298 (1976)
A. N. Brouers et al.

We claim:

1. A solid non biological substrate suitable for use in formation of bio-mechanical micro-structures with a biological cell species in a cell support medium and providing an electrical connection to said cell species, said substrate having an extended generally planar surface of an electrically insulating material with a plurality of elongate topographical surface discontinuities providing cell-adhesion orienting zones having a width of from 0.2 to 10 micrometers but less than twice the width of a cell of said cell species and having a radius of curvature of at least 20 micrometers in a predetermined relation to each other and substantially spaced apart laterally from each other so that cells of said cell species attached to the substrate at one of said zones of the substrate are substantially remote from the cells in another one of said zones, and wherein there is provided at least one electrode in association with at least one of said discontinuities, which electrode is formed and arranged so as to be non-recessed relative to a cell position defined by said at least one discontinuity and in substantially direct proximity to said at least one discontinuity so as to facilitate electrical connection between said electrode and a said cell of said cell species attached to said at least one discontinuity without substantial distortion of said cell.

2. A solid non-biological substrate suitable for use in the formation of bio-mechanical micro-structures with a biological cell species in a cell support medium and providing an electrical connection to said cell species said substrate having an extended generally planar surface of an electrically insulating material with at least one elongate topographical surface discontinuity providing a cell-adhesion orienting zone having a width of from 0.2 to 10 micrometers but less than twice the width of a cell of said cell species and having a radius of curvature of at least 20 micrometers, at which zone is provided at least one electrode projecting from the surface of said surface discontinuity, said projecting electrode being formed and arranged so as to be non-recessed relative to a cell position defined by said at least one discontinuity and in substantially direct proximity to said at least one discontinuity so as to facilitate electrical connection between said electrode and a said cell of said cell species attached to said at least one discontinuity without substantial distortion of said cell.

3. A solid non-biological substrate as claimed in claim 2 wherein said electrode projects up not more than 0.5 micrometers from a said cell adhesion orienting zone at a said at least one discontinuity.

4. A substrate as claimed in claim 1 wherein said discontinuities are in the form of ridges.

5. A substrate as claimed in claim 4 wherein at least one of said discontinuities is rectilinear.

6. A substrate as claimed in claim 1 wherein said discontinuities are in the form of grooves.

7. A substrate as claimed in claim 2 wherein said discontinuities are in the form of ridges.

8. A substrate as claimed in claim 2 wherein said discontinuities are in the form of grooves.

9. A substrate as claimed in claim 1 wherein:
said electrode includes an exposed portion, which exposed portion is formed and arranged to be substantially enclosable by a cell of said cell species thereby substantially to prevent current leakage from the electrode to the cell support medium during use of the substrate.

10. A substrate as calimed in claim 2 wherein:
said electrode includes an exposed portion, which exposed portion is formed and arranged to be substantially enclosable by a cell of said cell species thereby substantially to prevent current leakage from the electrode to the cell support medium during use of the substrate.

* * * * *